United States Patent
Orbay et al.

(10) Patent No.: US 7,001,388 B2
(45) Date of Patent: Feb. 21, 2006

(54) SYSTEM FOR STABILIZATION OF FRACTURES OF CONVEX ARTICULAR BONE SURFACES INCLUDING SUBCHONDRAL SUPPORT STRUCTURE

(75) Inventors: Jorge L. Orbay, Miami, FL (US); Javier E. Castaneda, Miami, FL (US); Cesare Cavallazzi, Miramar, FL (US)

(73) Assignee: Hand Innovations, LLC, Miami, FL (US)

( * ) Notice: Subject to any disclaimer, the term of this patent is extended or adjusted under 35 U.S.C. 154(b) by 0 days.

(21) Appl. No.: 11/040,734

(22) Filed: Jan. 21, 2005

(65) Prior Publication Data

US 2005/0165395 A1 Jul. 28, 2005

Related U.S. Application Data

(60) Provisional application No. 60/546,127, filed on Feb. 20, 2004, provisional application No. 60/538,589, filed on Jan. 23, 2004.

(51) Int. Cl.
*A61B 17/80* (2006.01)

(52) U.S. Cl. .......................................... 606/69; 606/72
(58) Field of Classification Search ................ 606/60, 606/65, 66, 67, 68, 69, 70, 71, 72, 73
See application file for complete search history.

(56) References Cited

U.S. PATENT DOCUMENTS

| | | | |
|---|---|---|---|
| 2,500,370 A | 3/1950 | McKibbin | |
| 3,489,143 A | 1/1970 | Halloran | |
| 4,794,919 A | 1/1989 | Nilsson | |
| 4,858,602 A | 8/1989 | Seidel et al. | |
| 5,180,383 A | 1/1993 | Haydon | |
| 5,190,544 A | 3/1993 | Chapman et al. | |
| 5,458,654 A | 10/1995 | Tepic | |
| 5,472,444 A | 12/1995 | Huebner et al. | |
| 5,578,035 A | 11/1996 | Lin | |
| 5,676,667 A | 10/1997 | Hausman | |
| 5,709,686 A | 1/1998 | Talos et al. | |
| 5,749,872 A | 5/1998 | Kyle et al. | |
| 5,776,194 A | 7/1998 | Mikol et al. | |
| 5,931,839 A | 8/1999 | Medoff | |
| 6,096,040 A | 8/2000 | Esser | |
| D443,060 S | 5/2001 | Benirschke et al. | |
| 6,270,499 B1 | 8/2001 | Leu et al. | |
| 6,358,250 B1 | 3/2002 | Orbay | |
| 6,364,882 B1 | 4/2002 | Orbay | |

(Continued)

FOREIGN PATENT DOCUMENTS

| | | |
|---|---|---|
| DE | G 92 00 328.1 | 4/1992 |
| FR | 2606268 | 5/1988 |

OTHER PUBLICATIONS

Zimmer Periarticular Plating System-Low-Profile Fixation (catalog). Zimmer, Inc., 2003. (8 pages).

(Continued)

*Primary Examiner*—David O. Reip
(74) *Attorney, Agent, or Firm*—Gordon & Jacobson, P.C.

(57) ABSTRACT

A fracture fixation system is provided for a fracture of a head portion of a long bone which has subchondral bone defining a convex articular surface. The system includes a plate element positionable on the long bone substantially opposite the head portion of the long bone and on a first side of the fracture, and a post coupled to the plate and into the head portion of the bone and across the fracture. A cross peg is coupled to the post to provide support of the subchondral bone.

7 Claims, 6 Drawing Sheets

U.S. PATENT DOCUMENTS

| | | |
|---|---|---|
| 6,379,359 B1 | 4/2002 | Dahners |
| 6,409,768 B1 | 6/2002 | Tepic et al. |
| 6,440,135 B1 | 8/2002 | Orbay et al. |
| 6,468,278 B1 | 10/2002 | Muckter |
| 6,623,486 B1 | 9/2003 | Weaver et al. |
| 6,866,665 B1 | 3/2005 | Orbay |
| 2005/0010226 A1 | 1/2005 | Grady, Jr. et al. |

OTHER PUBLICATIONS

The Mayo Clinic Congruent Elbow Plates (catalog). ACUMED. Hillsboro, OR: 2003. (20 pages).

Locking Compression Plate (LCP) System (brochure). SYNTHES. West Chester, PA: 2003. (6 pages).

Two non-published pages of sketches made by Eduardo Gonzalez-Hernandez (intialed 'egh') in Miami, FL on Nov. 12, 2003, provided to inventor on that date.

SYSTEM FOR STABILIZATION OF FRACTURES OF CONVEX ARTICULAR BONE SURFACES INCLUDING SUBCHONDRAL SUPPORT STRUCTURE

CROSS-REFERENCE TO RELATED APPLICATIONS

The application claims the benefit of U.S. Provisional Application No. 60/538,589, filed Jan. 23, 2004 and 60/546,127, filed Feb. 20, 2004.

BACKGROUND OF THE INVENTION

1. Field of the Invention

This invention relates broadly to surgical devices. More particularly, this invention relates to a fracture fixation system including an orthopedic plate and associated fasteners for fastening the plate to the bone and tendons.

2. State of the Art

The proximal humerus comprises the upper portion of the humerus, i.e. upper arm of the human body, commonly known as the shoulder area. Fractures of the proximal humerus typically result from traumatic injuries such as sporting accidents and can be more frequent with age due to bone loss. Fractures of the proximal humerus are treated by exposing the fracture site and reducing the bone fracture and then placing a plate or other means onto the bone to fixate the fracture for healing in the reduced position. Reducing the fracture includes realigning and positioning the fractured portions of the bone to their original position or similar stable position. Fixating the fracture includes positioning a plate over the fractured portions and securing the plate onto the fractured bones and adjacent non-fractured bones with bone screws.

Conventional fixation plates have several shortcomings when applied to the proximal humerus. In general, they are not well shaped for the humeral anatomy, and when provided in a size necessary to provide the structural rigidity for stability of a humeral fracture are not easily shaped by the surgeon. Furthermore, such plates require large screws which do not provide purchase in underlying osteoporotic bone.

Two plates particularly contoured for the proximal humerus are the locking proximal humeral plate (LPHP) and PHILOS from Synthes of Paoli, Pa. These plates include a proximal head portion which receives several fixed angle fasteners which extend into the rounded head of the humerus perpendicular to the articular surface and threadably couple to the plate. Particularly in osteoporotic bone, there is a tendency for the fasteners to pierce the bone and enter the articular space between the head of the humerus and the shoulder socket which can cause significant irritation and potentially greater orthopedic damage. Such damage can interfere with, prolong, or prevent proper healing of the humeral fracture, in addition to causing the patient additional pain and the development of post-traumatic arthritis.

SUMMARY OF THE INVENTION

It is therefore an object of the invention to provide a humeral fracture fixation system which is anatomically appropriate for the humerus.

It is another object of the invention to provide a humeral fracture fixation system which provides a stable framework for support of a proximal humeral fracture.

It is a further object of the invention to provide a humeral fracture fixation system in which the fasteners extending through the plate will not break through the articular surface.

It is also object of the invention to provide a humeral fracture fixation system which facilitates alignment of fasteners into the head of the humerus.

It is yet another object of the invention to provide a humeral fracture fixation system which provides the surgeon a tactile sensation of when fasteners are properly implanted within the head of the humerus.

In accord with these objects, which will be discussed in detail below, a humeral fracture fixation system is provided and includes a plate, a plurality of cortical screws, and a plurality of posts, cross pegs, and set screws for coupling the plate to the humerus and stabilizing the fracture. The system preferably also includes K-wires and suture material, as discussed below.

The plate includes a plurality of post holes. A post is provided for each post hole, and extends through the head portion of the plate generally perpendicular to the articular surface of the shoulder. According to a preferred aspect of the invention, each post includes a head which preferably can be fixed in a particular rotational orientation relative to the post hole. The post also includes a plurality of transverse, preferably parallel holes longitudinally displaced along its shaft. The post preferably further includes an axial bore which extends at least to the furthest transverse hole, and an internal thread below a driver recess. Preferably through use of an alignment jig, a cross peg can be extended through a hole drilled into the bone and through one of the transverse holes of a post. The hole is preferably not drilled completely through the head of the humerus. During insertion, the cross peg is subject to little resistance and the surgeon has tactile sensation as to when the cross peg has been extended through the appropriate transverse hole and when the end of the cross peg has reached cortical bone. The cross peg is optionally provided with a threaded head for engagement with the cancellous bone, but such is not required. A set screw of appropriate length is then inserted through the axial bore of the post until the set screw contacts the shaft of the cross peg where the cross peg extends through the transverse hole of the post. The set screw is threadably locked relative to the post to exert pressure on the cross peg and thereby retain the cross peg. Set screws of various lengths may be provided, or alternatively common length set screws may be cut down in size, if necessary, to the appropriate prior to insertion through a post.

According to another preferred aspect of the invention, the head portion includes a plurality of alignment holes which are sized to closely receive individual K-wires in a particular orientation. The orientation of axes through the alignment holes, and consequently K-wires inserted therethrough, closely conforms to the space defined by the posts when coupled to the head portion of the plate.

After the fracture is reduced and prior to drilling holes for the posts, the surgeon drills K-wires through the alignment holes on the head portion of the plate to temporarily fix the orientation of the head of the plate to the head of the humerus. Once the alignment is so fixed, the fracture is examined, e.g., under fluoroscopy, to determine whether the fracture is reduced in an anatomically correct manner and if the K-wires are properly aligned relative to the anatomy. The fluoroscopically viewed K-wires provide an indication as to whether the posts will be properly oriented in relation to the fracture and articular surface. If the placement is correct, the K-wires maintain the position of the plate over the fracture while holes are drilled for the posts. If placement is not optimal, the K-wires can be removed and the surgeon has an opportunity to relocate and/or reorient the K-wires and drill again. Since each K-wire is of relatively small diameter, the bone is not significantly damaged by the drilling process and the surgeon is not committed to the initial drill location and/or orientation. Once the plate is properly positioned with the K-wires, the plate, posts, and cross pegs can be implanted as discussed above, and the K-wires can be removed.

According to yet another preferred aspect of the invention, the head portion includes a lower proximal recess and a plurality of suture holes thereabout. The recess raises the proximal head portion of the plate off the surface of the bone to allow the surgeon to pass a needle with suture material through the suture holes and between the plate and the bone to permit tendon and bone fragments to be sutured to the plate.

With the fixation system implanted, the posts are oriented perpendicular to the articular surface but do not extend far enough to break through the articular surface.

The cross pegs extend through the transverse holes in the posts and are oriented parallel to the articular surface to provide a structure which locks the plate relative to the bone. Furthermore, such orientation of the cross pegs will not result in any damage to, irritation to, or interference with the articular surface of the shoulder joint.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
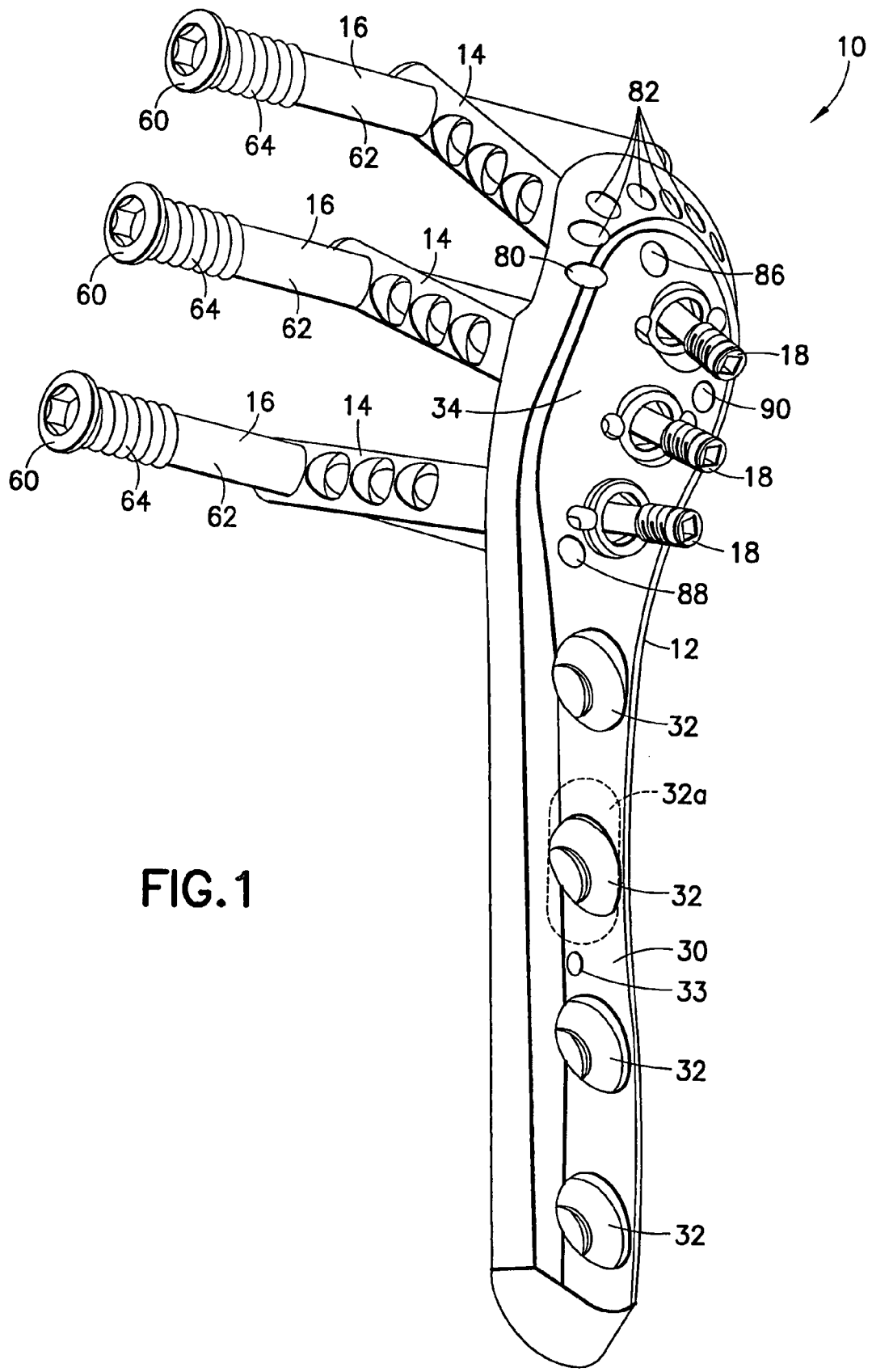
FIG. 1 is a perspective of a first embodiment of a proximal humeral fracture fixation system according to the invention, shown with a humeral plate, posts, transverse cross pegs, and set screws.

Turning now to FIGS. 1 through 4, a first embodiment of a proximal humeral fixation system 10 for fixation of a humeral fracture 11 (FIG. 4) of the left arm is shown. The system 10 includes a humeral plate 12, and a plurality of rigid posts 14, rigid cross pegs 16, set screws 18, and cortical screws 19, all for coupling the plate 12 to the humerus 20 (FIG. 4) and stabilizing the fracture. The system 10 preferably also includes K-wires 22 and suture material 24, as discussed below.

Figure 2:
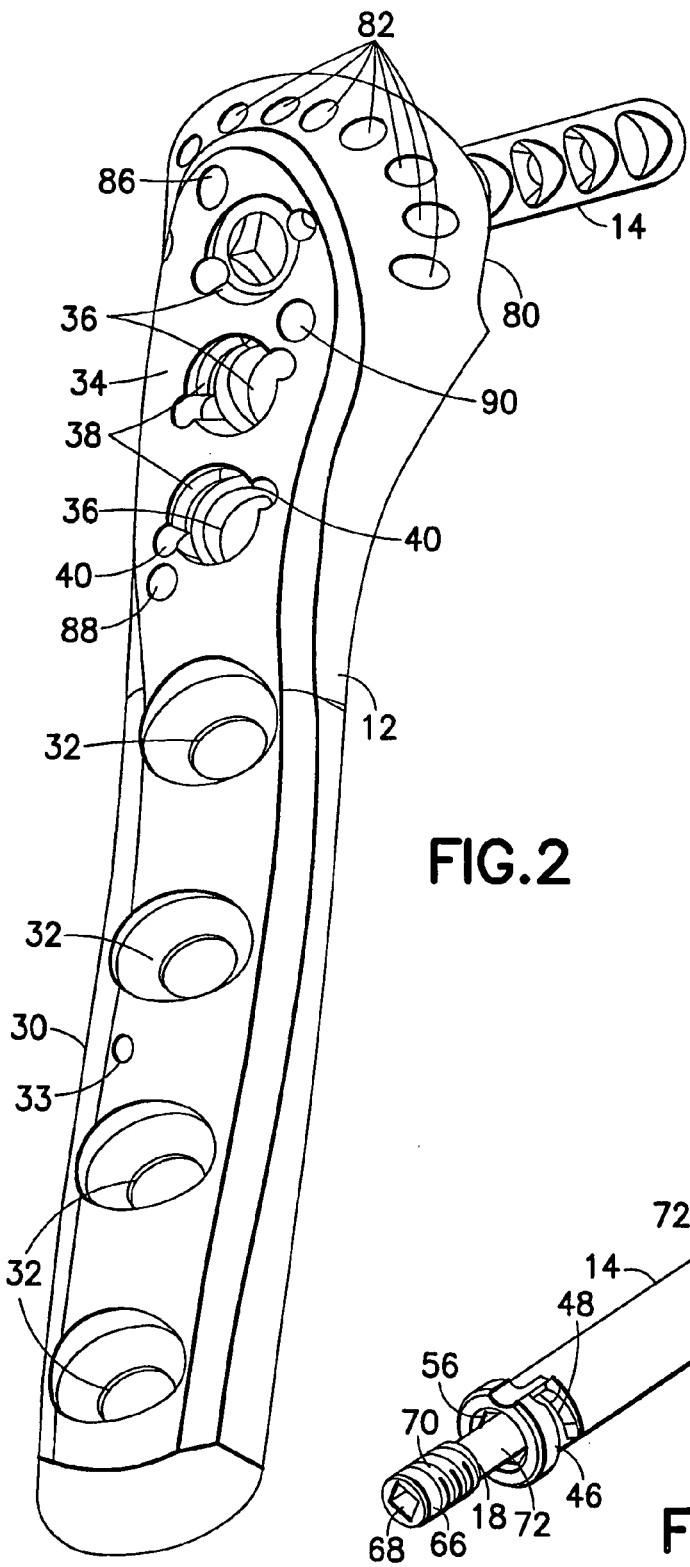
FIG. 2 is another perspective view of the first embodiment of FIG. 1, showing the humeral plate provided with one fixation post.
Figure 3:
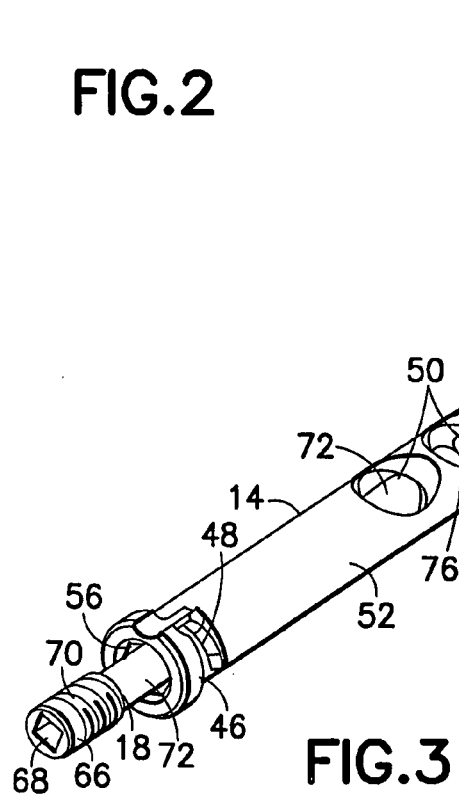
FIG. 3 is a perspective view showing the relationship between a fixation post, a transverse cross peg, and a set screw.

Referring to FIGS. 1 through 3, the humeral plate 12 has a shaft portion 30 and a head portion 34. The head portion 34 is angled slightly relatively to the shaft portion to properly seat on the humeral anatomy. The shaft portion 30 includes screw holes 32, one of which may be slotted or oblong (as indicated by dotted line 32a in FIG. 1) to permit the plate 12 to be longitudinally moved relative to a screw placed therethrough. The shaft portion may also include one or more K-wire holes 33. The head portion 34 is provided with post holes 36. As indicated by the posts 14 in FIG. 1, axes through the post holes 36 are preferably substantially in a common plane but preferably diverge from each other within the common plane. According to a preferred embodiment, the plane is in 10° retroversion relative to a frontal and vertical plane. Referring to FIG. 2, the post holes 36 define a locking structure 38, discussed in more detail below. In addition, tangential to each post holes 36 on diametrically opposite sides thereof are slots 40 for receiving an alignment jig (not shown) to aid in drilling respective holes for cross pegs 16.

Figure 4:
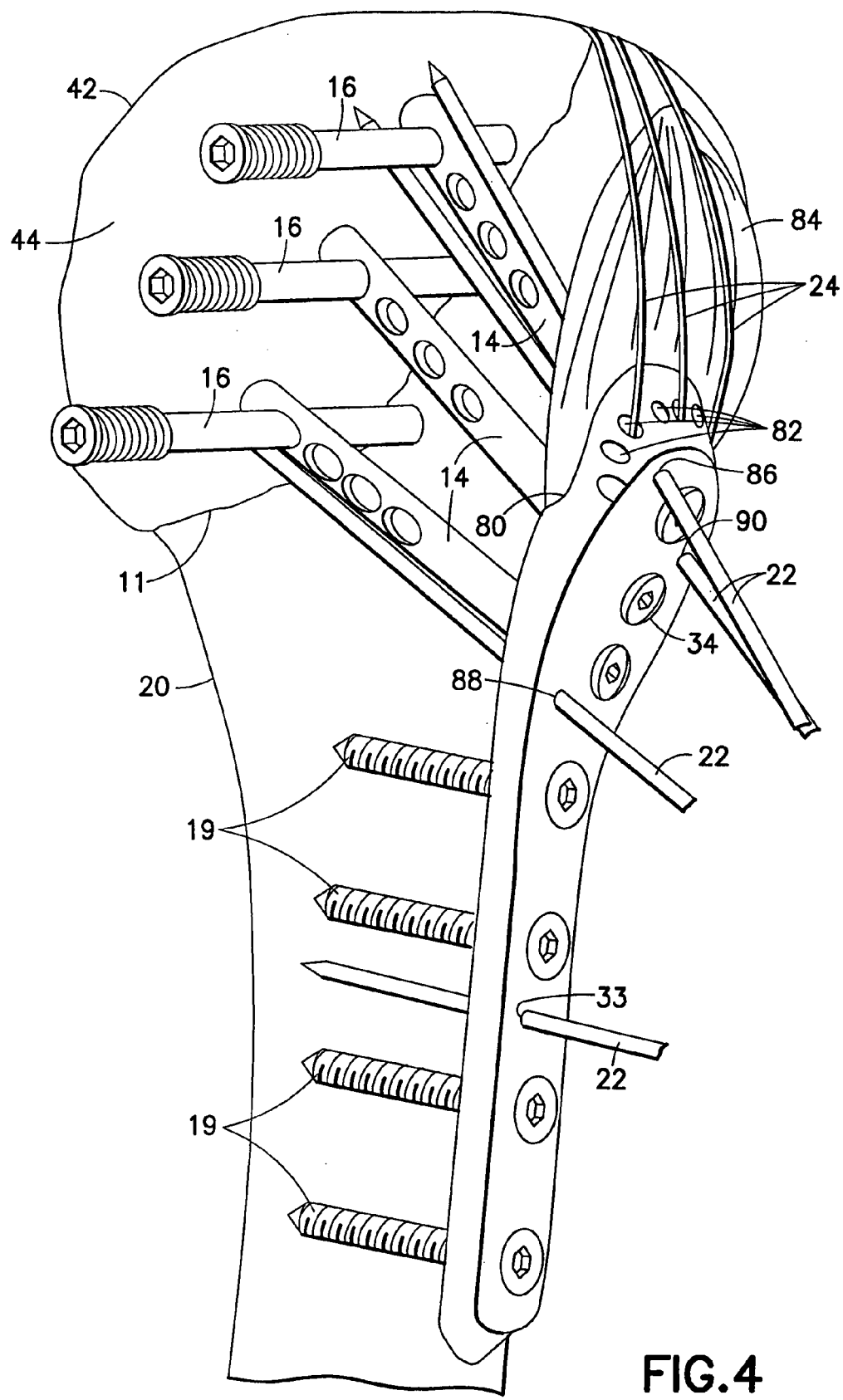
FIG. 4 illustrates the first embodiment of the proximal humeral fracture fixation system implanted on the humerus to stabilize a fracture.

Referring to FIGS. 1 through 4, a tubular post 14 is provided for each post hole 36, and extends through the head portion 34 of the plate 12 generally perpendicular to the articular surface 42 of the humeral head 44 (FIG. 4). According to a preferred aspect of the invention, each post 14 includes a head portion 46 with slots 48 which lock in a particular rotational orientation relative to the locking structure 38 of the post hole 36, similar to a bayonet lock. It is preferable that each post 14 be locked relative to the plate 12 without a threaded coupling therebetween, because it is difficult to machine a threaded coupling in which (i) the components are both fixedly and rigidly coupled together, and (ii) in which the rotational orientation of the post can be predetermined with certainty upon locking. In accord with a preferred aspect of the present embodiment, the lock between a post 14 and its respective post hole 36 preferably occurs within less than one complete rotation of the post 14 relative to the post hole 36, and more preferably within 90° rotation. Notwithstanding the above, it is certainly possible to machine a threaded coupling between the post and the plate with the entry and termination points arranged and with the required tolerances to obtain the same results; i.e., predetermined rotational orientation upon fully seating the post in the plate. The post 14 also includes a plurality of transverse, preferably parallel holes 50 longitudinally displaced along the shaft 52 of the post 14. The post 14 further includes an axial bore 54 which extends from the head portion 46 at least to the furthest transverse hole 50, and an internal thread (not shown) below a driver recess 56 and preferably below the slots 48.

The cross pegs 16 each include a head 60 for receiving a driver, and a shaft portion 62. The shaft portion 62 is optionally threaded at 64 adjacent the head 60 for engagement with cancellous bone, but such is not required. The cross pegs 16 can be extended through a transverse hole 50 in a post 14 in the anterior-posterior plane and locked in place with a set screw 18.

Referring to FIG. 3, the set screw 18 includes a head 66 with a driver recess 68 and external threads 70, and a shaft 72. A set screw of appropriate length is inserted through the axial bore 54 of the post 14 until the end 76 of the set screw 18 contacts the portion of the shaft 62 of the cross peg 16 extending through a transverse hole 50 of the post 14. The set screw 18 is threadably locked relative to the post 14 to exert pressure on the cross peg 16 and thereby retain the cross peg 16. Set screws 18 of various lengths may be provided for locking cross pegs in any of the longitudinally displaced transverse holes. Alternatively common length set screws may be cut down in size, if necessary, to the appropriate length prior to insertion through the bore 54 of a post 14. Where common length set screws 18 are provided, the set screws 18 may be scored along the shaft 72 to facilitate breaking or cutting the set screws to appropriate length. In yet another alternative, the cross pegs may include transverse holes through which the set screws can be passed. In that manner common length set screws can be used, provided the cross pegs are rotationally aligned to receive the set screws through the transverse holes.

Referring to FIGS. 2 and 4, according to another aspect of the invention, the head portion 34 of the plate 12 includes a lower proximal recess 80 and a plurality of suture holes 82 thereabout. The recess 80 raises the proximal portion of the head portion 34 of the plate 12 off the surface of the bone (as shown in FIG. 4) to allow the surgeon to pass a needle (not shown) with suture material 24 through the suture holes 82 and between the plate 12 and the bone 20. In this manner, suture material 24 can be used to secure tendons 84 of the rotator cuff to the plate 12 to place retaining force on smaller fragments of the fracture. The suture material 24 is preferably metal braid or cable.

According to yet another aspect of the invention, the head portion 34 includes a plurality of alignment holes 86, 88, and 90 which are sized to closely receive individual K-wires in a particular orientation. The orientation of axes through the alignment holes 86, 88 and 90, and consequently K-wires 22 inserted therethrough, closely conforms to the space defined by the posts 14 when coupled to the head portion 34 of the plate 12. More particularly, proximal alignment hole 86 is located to define an axis which corresponds to the anterior-superior boundary of the posts 14, distal alignment hole 88 is located to define an axis which corresponds to the anterior-inferior boundary of the posts 14, and relatively central alignment hole 90 is located to define an axis which corresponds to the posterior boundary of the posts 14. Similar use of alignment holes and K-wires is discussed in detail in co-owned U.S. Ser. No. 10/689,797, which is incorporated by reference herein in its entirety.

In view of the above, according to a method of stabilizing a fracture according to the invention, the fracture is reduced and the humeral plate 12 is placed on the proximal humerus in an apparently appropriate location, with the head portion 34 generally opposite the articular surface 42. The head portion 34 is then tacked onto the humeral head 44 with K-wires 22 drilled through the alignment holes 86, 88, 90, and the shaft portion 30 is preferably tacked to the distal fragment with one or more K-wires 22, through K-wires holes 33 in the shaft portion, or with one or more screws 19 in the screw holes 32. The fracture and location of the K-wires 22 are examined, e.g., under fluoroscopy, to determine whether the fracture is reduced in an anatomically correct manner and if the K-wires 22 are properly aligned relative to the anatomy. As indicated above, the fluoroscopically viewed K-wires 22 provide an indication as to whether the posts 14 will be properly oriented in relation to the fracture and the articular surface of the subchondral bone. If placement is not optimal, the K-wires 22 can be removed and the surgeon has an opportunity to relocate and/or reorient the K-wires 22 and drill again. Since each K-wire 22 is of relatively small diameter relative to the posts 14, the bone is not significantly damaged by the drilling process and the surgeon is not committed to the initial drill location and/or orientation.

Alternatively, shaft portion 30 fixation may be delayed until after placement of the head portion 34 of the plate 12 is determined to be desirable (via visualization of the K-wires), and then preferably at least one cortical screw 19 is inserted through a screw hole 32 to stabilize the shaft portion 30 to the humerus 20.

Holes are then drilled through the post holes 36 of the head portion 34 of the plate 12 for the posts 14. The holes are drilled across fracture 11. The drill bit for drilling holes through the posts 14 corresponds in diameter to the post holes 36 such that no alignment jig is necessarily required, although one may be used is desired. The holes are drilled through the relatively soft spongy bone of the humeral head 44 until the surgeon can 'feel' the harder cortex of the subchondral bone of the articular surface 42. All posts holes may be drilled before proceeding. Alternatively, one post hole may be drilled, and for that post hole, a post can be inserted therein and coupled to the plate, an associated cross peg hole can be drilled, and a cross peg can be coupled to the post, as described in more detail below, prior to proceeding to drill the other post holes.

Assuming all post holes have been drilled, the posts 14 are then inserted through the post holes 36, and rotated to lock the heads 46 of the posts 14 relative to the locking structure 38 of the head portion 34 of the plate 12. In contrast to a conventional threaded coupling, the locking coupling of 46 and 38 constrains the transverse holes 50 to be in a predetermined rotational orientation relative to the plate 12. A jig (not shown) is then coupled to the internal threads of a post 14 and rotationally aligned relative to the tangential slots 40 of the post hole 36 to align a guide for drilling a hole in alignment with one of the transverse holes 50 of that post 14. Alternatively, the jig may be coupled directly the plate 12. Once the hole is drilled into the bone, the jig is removed. A cross peg 16 is then inserted through the drilled hole and extended through the transverse hole 50 of that post 14 such that the cross peg 16 extends parallel to the articular surface 42 of the humeral head 44 on the opposite side of the fracture 11 from the plate 12.

The particular transverse hole 50 in which a particular cross peg 16 is inserted can be determined by the surgeon based upon the size of the humeral head 44 and the location of the fracture. More particularly, it is desirable for each cross peg 16 to extend just below the articular surface 42. If the cross peg 16 is within the articular surface 42 it will cause interference with the joint. If the cross peg 16 is too far away from the articular surface 42, there will be too much spongy bone between the hard articular surface 42 and the cross peg 16 which could cause the fractured humeral head 44 to collapse. During insertion of the cross pegs 16, the cross pegs 16 are subject to little resistance through the drilled holes and the surgeon has tactile sensation as to when the cross pegs 16 have been extended through the appropriate transverse holes 50 and when the ends of the cross pegs have reached hard cortical bone. It is undesirable to force the cross pegs through the cortical bone such that the ends of the cross pegs 16 are exposed.

Once the cross peg 16 is properly positioned, it is desirable to lock it in position. The set screw 18 is inserted through the axial bore 54 of the post 14 and threadably coupled to the post 14 such that the end of the set screw 18 seats against the cross peg 16 locking the cross peg in place. The process is repeated for the other posts 14 and cross pegs 16.

The K-wires 22 are removed. The sutures 24 are added, and the remaining cortical screws 19, if not already inserted, are inserted to further stabilize the fracture.

With the fixation system implanted, the posts 14 are oriented perpendicular to the articular surface 42 but do not extend far enough to break through the articular surface. The plate 12 and cross pegs 16 sandwich the fracture 11 to provide a stabilizing framework. The cross pegs 16 extending through the transverse holes 50 in the posts 14 are oriented parallel to the articular surface 42 and provide a structure which locks the plate relative to the bone. Furthermore, such placement and orientation of the cross pegs 16 will not result in any damage to, irritation to, or interference with the articular surface of the shoulder joint.

Figure 5:
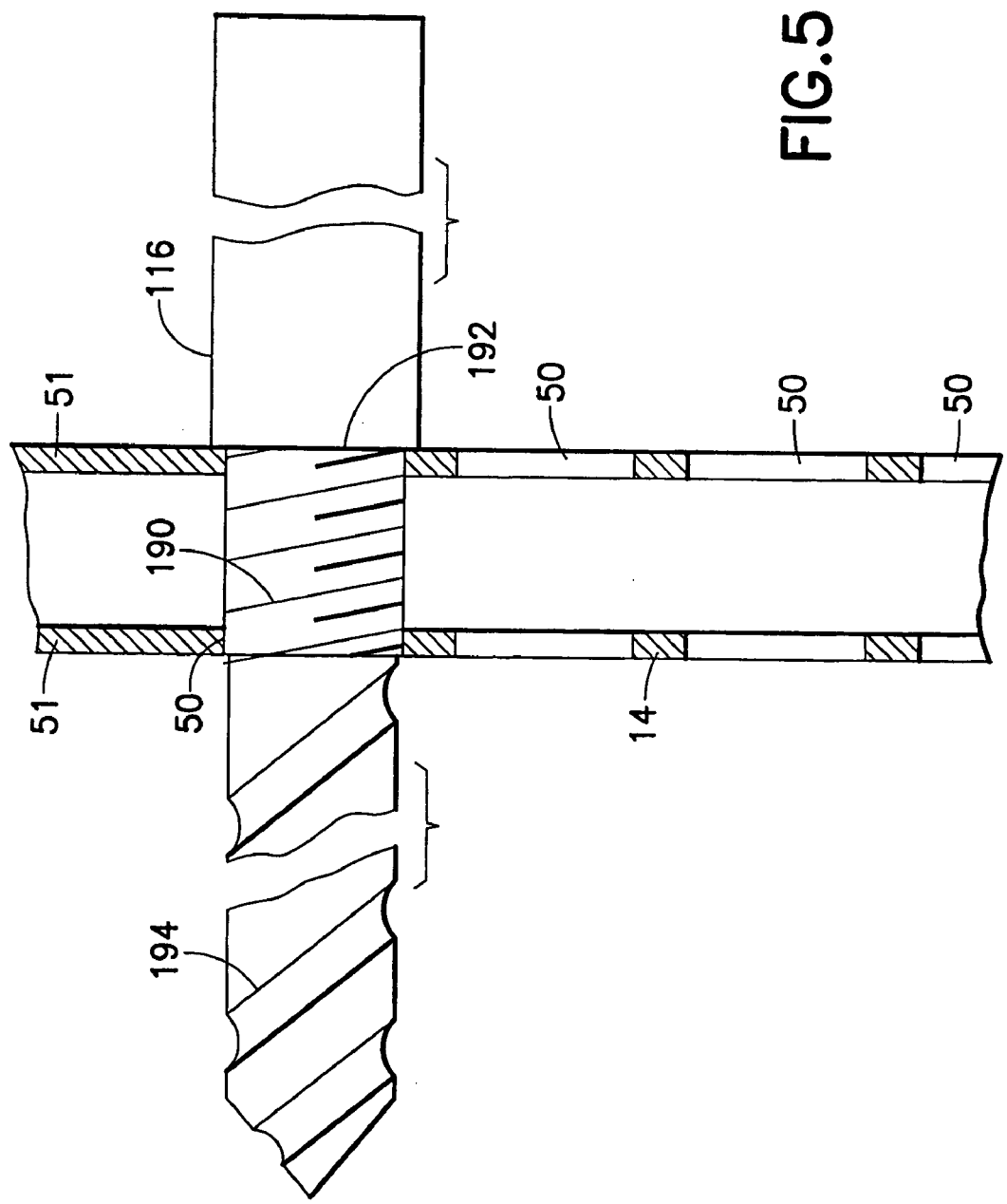
FIG. 5 is a schematic view of an alternate embodiment of a cross peg for use in a fixation system according to the invention.

Referring now to FIG. 5, an alternative embodiment of a cross peg 116 for the fracture fixation system is shown. In the alternative embodiment, no set screw is required to secure the cross peg within the post. The cross peg 116 includes threads 190 along a central portion of its shaft which are preferably self-tapping and spaced appropriately to engage the wall 51 surrounding the holes 50 of the post 14. However, this threaded engagement may limit the surgeon's tactile sensation of when the far cortex is reached by the cross peg. In view thereof, the cross peg 116 may be provided with a shoulder 192 that limits its introduction, i.e. such that the shoulder 192 can not extend through the transverse hole 50. In addition, the cross peg 116 may include cutting flutes 194 which permit drill-less introduction.

As yet another alternative, the transverse holes may be provide with machine threads, and the cross pegs may be likewise threaded with machine threads such that the cross peg and post can threadably engage together without the cross peg tapping into the post.

Furthermore, any of the above described cross pegs may be headless. In such a configuration, the cross peg is adapted to be seated beneath the surface of the bone. Thus, such a cross is suited to extend through the articular surface without interference with the shoulder joint if extension of a cross peg through the articular surface is necessary or desirable for stabilization of a particular fracture with the system of the invention.

Figure 6:
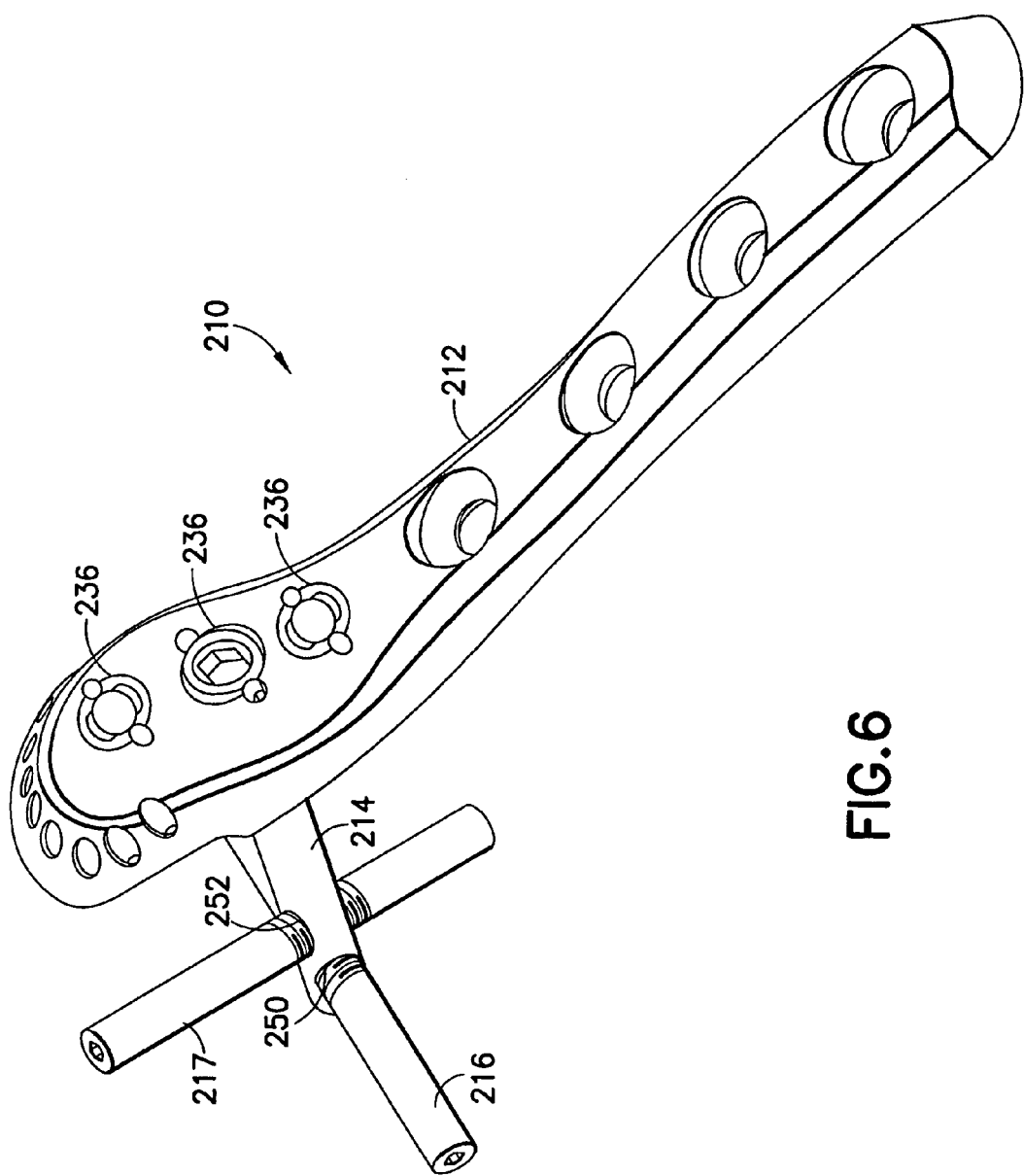
FIG. 6 is a perspective view of a second embodiment of a proximal humeral fixation system according to the invention.

Turning now to FIG. 6, another embodiment of humeral fracture fixation system 210 according to the invention is shown. In system 210, a single post 214 may be inserted through any of the post holes 236 in plate 212, although only a single post hole is required in this embodiment. The post 214 includes holes 250, 252 which are oriented transverse to each other, preferably at 90°, and preferably perpendicular to the longitudinal axis of the post 214. Cross pegs 216, 217 are then inserted through holes 250, 252 and preferably locked relative to the post. Cross peg 216 extends parallel to the anterior-posterior plane of the articular surface, and cross peg 217 extends parallel to the relatively transverse plane. In this embodiment, it is not practical to lock the distal cross peg 216 with a set screw. Thus, it may be desirable for one or both of the cross pegs to thread into or relative to the post 214. Cross pegs 216, 217 are also shown in a headless design, described above, which can be seated beneath the surface of the bone and provide no interference with the articular surface.

Figure 7:
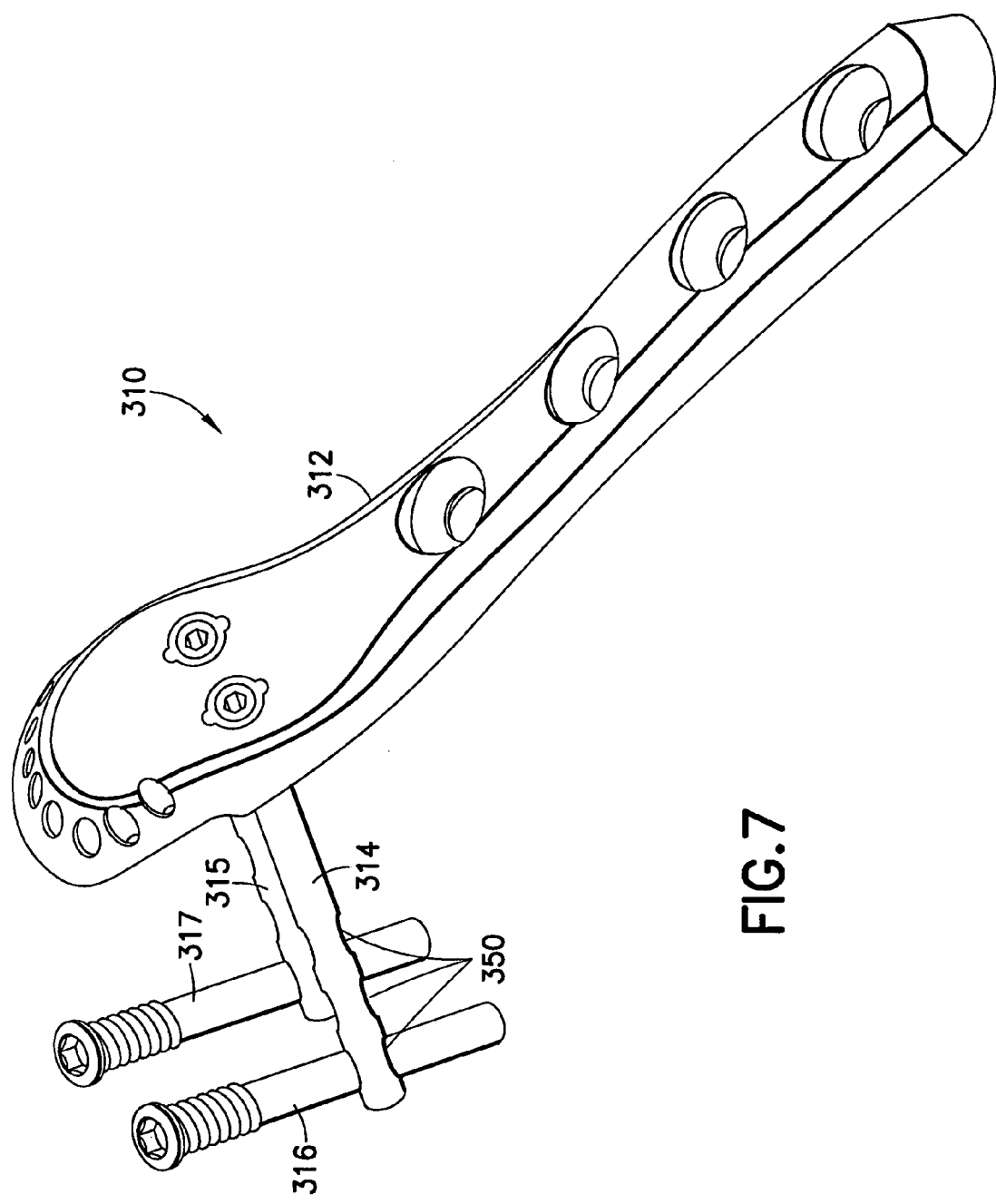
FIG. 7 is a perspective view of a third embodiment of a proximal humeral fixation system according to the invention.

Referring now to FIG. 7, another embodiment of humeral fracture fixation system 310 according to the invention is shown. In system 310, two posts 314, 315 are displaced in an anterior-posterior plane. The posts are preferably angled relative to each other in the same plane by, e.g., 20° to 90°. Alternatively, the posts 314, 315 may be vertically offset in the proximal-distal plane. Each of the posts 314, 315 has at least one transverse hole 350, with an axis therethrough preferably oriented substantially transverse to the anterior-posterior plane when the system 310 is implanted at the shoulder, and may have a plurality of such holes 350 longitudinally displaced along the post. A cross peg 316, 317 is inserted through a selected one of the holes 350 in each post 314, 315.

There have been described and illustrated herein embodiments of fracture fixation systems and methods of stabilizing a fracture, particularly of the humerus. While particular embodiments of the invention have been described, it is not intended that the invention be limited thereto, as it is intended that the invention be as broad in scope as the art will allow and that the specification be read likewise. Thus, while the preferred embodiments are for humeral fracture fixation systems, it is appreciated that the system is well adapted to bone fractures of any articular surface having a convex shape. Thus, the system of the invention could similarly be used to treat a fracture of the femoral head. In such variation, the angle between the head and shaft portions may be different so that the head portion properly seats on the anatomy. In addition, while a particular number of posts and cortical screws have been disclosed in relation to particular embodiments, it will be understood that only one post is required, and fewer or more cortical screw holes and/or screws than shown can be used. Furthermore, while cortical screws are disclosed for coupling the shaft portion to the bone, other fasteners can likewise be used. Moreover, while the terms 'posts' and 'pegs' have been used to described particular elements of the invention, it is understood that such terms are used as a matter of convenience, and are not intended to confer particular structure when used in the claims. Thus, what is referred to as a 'post' is intended to broadly read on any rigid shaft-like fastener mechanically coupled to, but not integral with the plate. Also, what is referred to as a 'peg' is intended to broadly read on any shaft-like element which extends in transverse relation one of the posts and is (i) coupled to such post and/or (ii) extends through a transverse hole formed within the post. Thus, the peg may be a screw, a non-threaded rod, a K-wire, etc. Furthermore, while left-hand humeral plates are shown, it is recognized that right-hand humeral plates are generally mirror-images of the illustrated left-hand plates. Moreover, while the system has been described for use with respect to fractures, it is appreciated that it may also be used in the treatment of osteotomies and non-unions of the proximal humerus and other bones having an articular surface with a convex shape. It will therefore be appreciated by those skilled in the art that yet other modifications could be made to the provided invention without deviating from its scope as claimed.

What is claimed is:

1. A proximal humeral fracture fixation system, comprising:
    a) a plate including first and second post holes;
    b) a firstpost mechanically coupled in said first post hole in a rotationally fixed manner;
    c) a first rigid cross support extending through a distal portion of said first post; and
    d) a second post mechanically coupled in said second post hole.

2. A proximal humeral fracture fixation system according to claim 1, further comprising:
    a second rigid cross support extending through a distal portion of said second post.

3. A proximal humeral fracture fixation system according to claim 1, wherein:

said first and second posts extend in an anterior-posterior plane.

4. A proximal humeral fracture fixation system according to claim 1, wherein:

said first and second posts extend in a proximal-distal plane.

5. A proximal humeral fracture fixation system, comprising:

a) a proximal humeral plate including a head portion with a post hole and a shaft portion with at least one bone screw hole;

b) a post insertable into said post hole and including a peg hole;

c) first means for rotationally fixing said post in said a post hole such that said peg hole is in a predetermined orientation; and d) a rigid cross peg extending through said peg hole.

6. A proximal humeral fracture fixation system according to claim 5, wherein:

wherein said cross peg extends in an anterior-posterior plane.

7. A proximal humeral fracture fixation system according to claim 5, wherein:

said post includes a plurality of peg holes, and said rigid cross peg can extend through any of said peg holes.

\* \* \* \* \*